United States Patent
McClanahan et al.

(10) Patent No.: US 6,190,644 B1
(45) Date of Patent: *Feb. 20, 2001

(54) DENTIFRICE COMPOSITIONS CONTAINING POLYPHOSPHATE AND MONOFLUOROPHOSPHATE

(75) Inventors: Stephen Francis McClanahan, Loveland; Donald James White, Jr., Fairfield; Edward Russell Cox, Germantown, all of OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/754,439

(22) Filed: Nov. 21, 1996

(51) Int. Cl.$^7$ ................................. A61K 7/16; A61K 7/18
(52) U.S. Cl. ................................. 424/52; 424/49
(58) Field of Search ........................ 424/49–58

(56) References Cited

U.S. PATENT DOCUMENTS

| | | | |
|---|---|---|---|
| 2,191,199 | * 2/1940 | Hall | 167/93 |
| 2,409,718 | * 10/1946 | Snell et al. | 252/102 |
| 2,498,344 | * 2/1950 | Rider et al. | 252/102 |
| 3,004,897 | * 10/1961 | Shore | 167/93 |
| 3,130,002 | 4/1964 | Fuchs | 21/2.7 |
| 3,562,385 | * 2/1971 | Block et al. | 424/54 |
| 3,932,603 | * 1/1976 | Haas | 424/49 |
| 3,934,002 | * 1/1976 | Haefele | 424/54 |
| 4,244,931 | * 1/1981 | Jarvis et al. | 424/57 |
| 4,247,526 | 1/1981 | Jarvis et al. | 423/266 |
| 4,357,318 | * 11/1982 | Shah et al. | 424/52 |
| 4,370,314 | * 1/1983 | Gaffar | 424/54 |
| 4,452,713 | 6/1984 | Small | 252/99 |
| 4,460,565 | 7/1984 | Westsrate et al. | 424/52 |
| 4,515,772 | 5/1985 | Parran, Jr. et al. | 424/57 |
| 4,528,181 | 7/1985 | Morton et al. | 424/52 |
| 4,627,977 | 12/1986 | Gaffar et al. | 424/52 |
| 4,913,895 | 4/1990 | Miyake et al. | 424/57 |
| 5,041,280 | * 8/1991 | Smigel | 424/52 |
| 5,094,844 | 3/1992 | Gaffar et al. | 424/52 |
| 5,096,701 | 3/1992 | White, Jr. et al. | 424/52 |
| 5,176,900 | 1/1993 | White, Jr. et al. | 424/52 |
| 5,192,532 | 3/1993 | Guay et al. | 424/53 |
| 5,236,696 | * 8/1993 | Catiis et al. | 424/49 |
| 5,256,402 | * 10/1993 | Prencipe et al. | 424/53 |
| 5,296,215 | * 3/1994 | Burke et al. | 424/49 |
| 5,296,217 | * 3/1994 | Stookey | 424/57 |
| 5,320,832 | * 6/1994 | Catiis et al. | 424/5 |
| 5,368,844 | 11/1994 | Gaffar et al. | 424/49 |
| 5,496,540 | 3/1996 | Gaffar et al. | 424/49 |
| 5,565,190 | * 10/1996 | Santaluga et al. | 424/53 |
| 5,571,501 | * 11/1996 | Toy | 424/49 |
| 5,599,525 | * 2/1997 | Hsu et al. | 424/49 |
| 5,601,803 | * 2/1997 | Masters et al. | 424/49 |
| 5,614,174 | * 3/1997 | Hsu et al. | 424/49 |
| 5,630,999 | * 5/1997 | Burke et al. | 424/49 |
| 5,648,064 | * 7/1997 | Gaffar et al. | 424/53 |
| 5,820,853 | * 10/1998 | Glandorf | 424/49 |
| 5,820,854 | * 10/1998 | Glandurf | 424/49 |
| 5,885,553 | * 3/1999 | Michael | 424/49 |
| 5,885,554 | * 3/1999 | Michael et al. | 424/49 |
| 5,939,052 | * 8/1999 | White et al. | 424/52 |
| 5,939,080 | * 8/1999 | Michael et al. | 424/49 |
| 5,980,869 | * 11/1999 | Sanjker et al. | 424/49 |

FOREIGN PATENT DOCUMENTS

| | | |
|---|---|---|
| 570803 | * 2/1959 | (CA). |
| 2 602 981 | * 7/1977 | (DE). |
| 490384 | * 8/1938 | (GB). |
| 94/14406 | * 7/1994 | (WO). |
| 94/14407 | * 7/1994 | (WO). |
| 95/09603 | * 4/1995 | (WO). |

OTHER PUBLICATIONS

Kerr, D. A., et al., "Sodium Hexametaphosphate as an Aid in the Treatment of Periodontal Disease", J. D. Res. 23:189, (1944), pp. 313–6.

Draus, F.M., et al., "Pyrophosphate and Hexametaphosphate Effects in In Vitro Calculus Formation", Archs Oral Biol., vol. 15 (1970), pp. 893–96.

U.S. application No. 08/754,577, White Jr., et al., Filed Nov. 21, 1996.

FMC Corp. (1980) FMC Glassy Phosphates–Sodaphos–Hexaphos–Glass H Pre–1980 Technical Data 12 pages.*

Stookey (II) Am. J. Vet. Sci. 56(7): 913–918 "Effect of Sodium Hexametaphosphate on Dental Calculaus Formation in Dogs" Jul. 1995.*

Shibata et al. Arch. Oral. Biol. 27:809–816 "Anti Bacterial Action of Condensed Phosphates on the Bacterium S. Mutans, Exp. Caries in the Hamster", 1982.*

Tanzer et al. Infection & Immunity 1(6): 604–606 "Polyphosphate Inhibition of Growth of Plaques Formed by Streptococli & Diptherig Implicated in Oral Disedse", Jun. 1970.*

Fosdick et al J. Dent. Res. 39: 630 "The Effect of Phosphates on the Acid Fermentation of Sugar Saliva Mixtures", 1960.*

Kurr et al J. Dent. Res. 23: 313–316 "Sodium Hexametaphosphate as an Aid in the Treatment of Periodontal Disease", 1944.*

Warren et al J. Periodont. 35:55/505–62–512 "Effects of Periodontal Disease and of Calculus Solvents on Microhardness of Cementum", 1964.*

Briner et al Calc. Tiss. Res. 11: 10–22 (1973) "In Vitro and In Vivo Evaluation of Anti–Calculus Agents", 1973.*

* cited by examiner

*Primary Examiner*—Shep K. Rose
(74) *Attorney, Agent, or Firm*—Emelyn L. Hiland; Angela M. Stone; Betty J. Zea

(57) ABSTRACT

Disclosed are oral compositions comprising one or more linear polyphosphates having an average chain length of about 4 or more, sodium monofluorophosphate, a buffering agent, an abrasive polishing material containing less than 23% calcium, and one or more aqueous carriers, wherein the oral composition has a total water content of from about 5% to about 20%.

14 Claims, No Drawings

DENTIFRICE COMPOSITIONS CONTAINING POLYPHOSPHATE AND MONOFLUOROPHOSPHATE

BACKGROUND OF THE INVENTION

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel, and dentine. An organic portion is also present and consists of desquamated epithelial cells, leukocytes, salivary sediment, food debris, and various types of microorganisms.

As the mature calculus develops, it becomes visibly white or yellowish in color unless stained or discolored by some extraneous agent. This is undesirable from an aesthetic standpoint.

Mechanical removal of calculus periodically by the dentist is routine dental office procedure. A variety of chemical and biological agents have also been suggested to retard calculus formation or to remove calculus after it is formed. Pyrophosphate salts are chemical agents known to have the ability to retard calculus formation as described, for example, in U.S. Pat. No. 4,999,184, to Parran, Jr. et al., issued Mar. 12, 1991, the disclosure of which is incorporated herein by reference in its entirety.

In addition to the pyrophosphate salts, other polyphosphates are also know to help retard calculus formation. U.S. Pat. No. 4,627,977, issued Dec. 9, 1986, to Gaffar et al. discloses the use of linear molecularly dehydrated polyphosphate salts combined with a fluoride ion-providing source and a synthetic linear polymeric polycarboxylate which inhibit enzymatic hydrolysis of the polyphosphate salt in saliva. U.S. Pat. No. 4,247,526, to Jarvis et al., issued Jan. 27, 1981, discloses the use of a pharmaceutically acceptable condensed phosphate salt in addition to dicalcium phosphate dihydrate and trimagnesium phosphate. Although polyphosphate containing oral care products are known, there is a continuing need to develop stable products containing polyphosphates.

The present inventors have discovered that certain polyphosphates, in particular, linear polyphosphates with average chain lengths greater than 4 will significantly react with most ionic fluoride sources in oral compositions and alter the pH of the oral compositions. This reaction compromises the ability of the oral composition to provide stable ionic fluoride and polyphosphate to the oral surfaces. The inventors have discovered that the polyphosphates do not react with monofluorophosphate, under normal manufacturing, storage, and use conditions. Therefore, in a single phase dentifrice composition, monofluorophosphate a suitable fluoride ion source to be present with the polyphosphate and still deliver a constant and similar source/amount of fluoride.

Therefore, it is an object of the present invention to provide stable single phase oral compositions comprising monofluorophosphate and polyphosphates. It is also an object of the present invention to provide oral compositions with improved antitartar activity through the use of polyphosphates.

These and other objects of the present invention will become readily apparent from the detailed description which follows.

All percentages and ratios used herein are by weight of the oral composition, unless otherwise specified. All measurements are made at 25° C., unless otherwise specified.

SUMMARY OF THE INVENTION

The present invention relates to an oral composition comprising an effective amount of one or more linear polyphosphates having an average chain length of about 4 or more, from about 0.15% to about 2.28% of sodium monofluorophosphate, an effective amount of a buffering agent, from about 6% to about 70% of an abrasive polishing material containing less than 23% calcium, and from about 40% to about 99% of one or more aqueous carriers; wherein the oral composition has a total water content of from about 5% to about 20%.

DETAILED DESCRIPTION OF THE INVENTION

The oral composition of the present invention may be in the form of a toothpaste or dentifrice. The term "dentifrice", as used herein, means paste, gel, or liquid formulations unless otherwise specified. The dentifrice composition may be in any desired form, such as deep striped, surface striped, multilayered, having the gel surrounding the paste, or any combination thereof. Alternatively, the oral composition may be one of the dentifrice compositions in a dual phase system comprising two dentifrice compositions contained in a physically separated compartment of a dispenser and dispensed side-by-side.

The term "dispenser", as used herein, means any pump, tube, or container suitable for dispensing toothpaste.

The term "oral composition" as used herein means the total dentifrice that is delivered to the oral surfaces. The oral composition is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity.

The term "aqueous carrier" as used herein means any safe and effective materials for use in the compositions of the present invention. Such materials include abrasive polishing materials, peroxide sources, alkali metal bicarbonate salts, thickening materials, humectants, water, surfactants, titanium dioxide, flavor system, sweetening agents, xylitol, coloring agents, and mixtures thereof.

The present compositions comprise essential components, as well as optional components. The essential and optional components of the compositions of the present invention are described in the following paragraphs.

Polyphosphate Source

The present invention includes a polyphosphate source. A polyphosphate is generally understood to consist of two or more phosphate molecules arranged primarily in a linear configuration, although some cyclic derivatives may be present. Although pyrophosphates are a polyphosphate, the polyphosphates desired are those having four or more phosphate molecules. The pyrophosphates are discussed separately. The inorganic polyphosphate salts desired include tetrapolyphosphate and hexametaphosphate, among others. Polyphosphates larger than tetrapolyphosphate usually occur as amorphous glassy materials. Preferred in this invention are the linear "glassy" polyphosphates having the formula:

XO(XPO$_3$)$_n$X wherein X is sodium or potassium and n averages from about 6 to about 125. Preferred are polyphosphates manufactured by FMC Corporation which are commercially known as Sodaphos (n≈6), Hexaphos (n≈13), and Glass H (n≈21). These polyphosphates may be used alone or in an combination thereof.

The phosphate sources are described in more detail in Kirk & Othmer, *Encyclopedia of Chemical Technology*, Fourth Edition, Volume 18, Wiley-Interscience Publishers (1996), incorporated herein by reference in its entirety, including all references incorporated into Kirk & Othmer. The polyphosphate source will typically comprise from about 0.5% to about 20%, preferably from about 4% to about 15%, more preferably from about 6% to about 10%, and most preferably from about 7% to about 9%, by weight of the oral composition.

Monofluorophosphate

The dentifrice composition of the present invention incorporates sodium monofluorophosphate. The oral compositions contain an amount of sodium monofluorophosphate that is capable of providing from about 50 ppm to about 3500 ppm, and preferably from about 500 ppm to about 3000 ppm of free fluoride ions. The sodium monofluorophosphate will be present in an amount of from about 0.15% to about 2.28% and preferably from about 0.30% to about 1.5%, by weight of the composition.

Buffering Agent

The present composition contains a buffering agent. If the oral composition is a dual phase system, a buffering agent will be present in both dentifrice compositions. Buffering agents, as used herein, refer to agents that can be used to adjust the pH of the compositions to a range of about pH 6.5 to about pH 10. These agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 1% to about 10%, and more preferably from about 1.5% to about 3%, by weight of the present composition.

Pyrophosphate Salt

Pyrophosphate salts may also be buffering agents. The pyrophosphate salts useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%, by weight of the composition. Free pyrophosphate ions may be present in a variety of protonated states depending on a the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 2.5% to about 8%, by weight of the composition. Some or all of the tetrasodium pyrophosphate maybe undissolved in the product and present as tetrasodium pyrophosphate particles. Pyrophosphate ions in different protonated states (e.g., $HP_2O_7^{-3}$) may also exist depending upon the pH of the composition and if part of the tetrasodium pyrophosphate is dissolved.

Compositions may also comprise a mixture of dissolved and undissolved pyrophosphate salts. Any of the above mentioned pyrophosphate salts may be used.

The pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

Optional agents to be used in place of or in combination with the pyrophosphate salt include such materials known to be effective in reducing calcium phosphate mineral deposition related to calculus formation. Agents included are synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS)], zinc citrate trihydrate, diphosphonates (e.g., EHDP; AHP), polypeptides (such as polyaspartic and polyglutamic acids), and mixtures thereof.

Aqueous Carriers

In preparing the present compositions, it is desirable to add one or more aqueous carriers to the compositions. Such materials are well known in the art and are readily chosen by one skilled in the art based on the physical and aesthetic properties desired for the compositions being prepared. Aqueous carriers typically comprise from about 40% to about 99%, preferably from about 70% to about 98%, and more preferably from about 90% to about 95%, by weight of the oral composition.

Abrasive Polishing Materials

An abrasive polishing material is generally included in the toothpaste compositions. The abrasive polishing material contemplated for use in the compositions of the present invention can be any material which does not excessively abrade dentin. The abrasive polishing material must have a calcium content of less than 23%. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962, incorporated herein by reference. Mixtures of abrasives may also be used. Only the abrasive polishing materials containing less than 23% calcium may be used in this single phase system.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, incorporated herein by reference. Silica abrasives described in U.S. patent application Ser. Nos., 08/434,147 and 08/434,149, both filed May 2, 1995, are also herein incorporated by reference. The abrasive in the toothpaste compositions described herein is generally present at a level of from about 6% to about 70% by weight of the composition. Preferably, toothpastes contain from about 10% to about 50% of abrasive, by weight of the oral composition.

Peroxide Source

The present invention may include a peroxide source. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the oral composition.

Additional Aqueous Carriers

The present invention compositions in the form of toothpastes, typically contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the dentifrice composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. The humectant generally comprises from about 0% to 70%, and preferably from about 15% to 55%, by weight of the composition.

Water employed in the preparation of commercially suitable oral compositions should preferably be of low ion content and free of organic impurities. The dentifrice composition will contain a water of from about 5% to about 20%, preferably from about 7% to about 14%, and more preferably from about 7% to about 12%, by weight of the composition. The amounts of water include the free water which is added plus that which is introduced with other materials, such as with sorbitol, silica, surfactant solutions, and/or color solutions.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sept. 27, 1977, incorporated herein by reference in its entirety. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the para-menthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

The present invention may also include xylitol. Xylitol is a sugar alcohol that is used as a sweetener and humectant. Xylitol may provide a therapeutic effect, such as an antibacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the total composition. Alternatively, if xylitol is used as a sweetener, it may be present at a lower level, such as from about 0.005% to about 5%, by weight of the dentifrice composition.

Sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is also a suitable water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis [4-(R-amino)-1-pyridinium] alkanes as disclosed in U.S. Pat. No. 4,206,215, issued Jun. 3, 1980, to Bailey, incorporated herein by reference. Stannous salts such as stannous pyrophosphate and stannous gluconate and other antimicrobials such as copper bisglycinate, copper glysinate, zinc citrate, and zinc lactate may also be included. Also useful are enzymes, including endoglycosidase, papain, dextranase, mutanase, and mixtures thereof Such agents are disclosed in U.S. Pat. No. 2,946,725, Jul. 26, 1960, to Norris et al. and in U.S. Pat. No. 4,051,234, Sept. 27, 1977 to Gieske et al., incorporated herein by reference. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al., incorporated herein by reference. These agents may be present at levels of from about 0.01% to about 1.5%, by weight of the composition.

The oral compositions of the present invention do not require a synthetic linear polymeric polycarboxylate at a level of about 0.05% or more, by weight of the composition. The synthetic linear polymeric polycarboxylates, as used herein, do not include known thickening agents including carboxymethylcellulose and other derivatives of cellulose and natural gum, as well as the carbopols.

Method of Treatment

The present invention compositions additionally relate to a method for reducing the incidence of calculus on dental enamel. The method of treatment herein comprises contacting the dental enamel surfaces in the mouth with the oral compositions according to the present invention.

EXAMPLES & METHOD OF MANUFACTURING

The following examples further describe and demonstrate embodiments within the scope of the present invention. These examples are given solely for the purpose of illustration and are not to be construed as limitations of the present invention as many variations thereof are possible without departing from the spirit and scope.

Example I

| Ingredient | Wt. % |
| --- | --- |
| Carboxymethycellulose | 0.60 |
| Water | 7.00 |
| Flavor | 1.00 |
| Glycerin | 25.44 |
| Poloxamer 407 | 5.00 |
| Propylene Glycol | 5.00 |
| Sodium Alkyl Sulphate[a] | 4.00 |
| Silica | 22.00 |
| Sodium Bicarbonate | 15.00 |
| Sodium Carbonate | 2.00 |
| Sodium Saccharin | 0.50 |
| Titanium Dioxide | 0.50 |
| Xanthan Gum | 0.20 |
| Glass H Polyphosphate | 7.00 |
| Polyethylene Glycol | 3.00 |
| Calcium Peroxide | 1.00 |
| Sodium Monofluorophosphate | 0.76 |

[a] 27.9% solution

Example II

| Ingredient | Wt. % |
| --- | --- |
| Carboxymethycellulose | 0.60 |
| Water | 7.00 |
| Flavor | 1.00 |
| Glycerin | 25.44 |
| Poloxamer 407 | 5.00 |
| Propylene Glycol | 5.00 |
| Sodium Alkyl Sulphate[a] | 4.00 |
| Silica | 22.00 |
| Sodium Bicarbonate | 15.00 |
| Sodium Carbonate | 2.00 |
| Sodium Saccharin | 0.50 |
| Titanium Dioxide | 0.50 |
| Xanthan Gum | 0.20 |
| Sodaphos Polyphosphate | 7.00 |
| Polyethylene Glycol | 3.00 |
| Calcium Peroxide | 1.00 |
| Sodium Monofluorophosphate | 0.76 |

[a] 27.9% solution

Example III

| Ingredient | Wt % |
| --- | --- |
| Carboxymethycellulose | 0.60 |
| Water | 7.00 |
| Flavor | 1.00 |
| Glycerin | 42.44 |
| Poloxamer 407 | 5.00 |
| Propylene Glycol | 5.00 |
| Sodium Alkyl Sulphate[a] | 4.00 |
| Silica | 20.00 |
| Sodium Carbonate | 2.00 |
| Sodium Saccharin | 0.50 |
| Titanium Dioxide | 0.50 |
| Xanthan Gum | 0.20 |
| Glass H Polyphosphate | 7.00 |
| Polyethylene Glycol | 3.00 |
| Calcium Peroxide | 1.00 |
| Sodium Monofluorophosphate | 0.76 |

[a] 27.9% solution

Example IV

| Ingredient | Wt. % |
| --- | --- |
| Carboxymethycellulose | 0.60 |
| Water | 7.00 |
| Flavor | 1.00 |
| Glycerin | 26.44 |
| Poloxamer 407 | 5.00 |
| Propylene Glycol | 5.00 |
| Sodium Alkyl Sulphate[a] | 4.00 |
| Silica | 22.00 |
| Sodium Bicarbonate | 15.00 |
| Sodium Carbonate | 2.00 |
| Sodium Saccharin | 0.50 |
| Titanium Dioxide | 0.50 |
| Xanthan Gum | 0.20 |
| Glass H Polyphosphate | 7.00 |
| Polyethylene Glycol | 3.00 |
| Sodium Monofluorophosphate | 0.76 |

[a] 27.9% solution

The dentifrice compositions are prepared as follows. Add the water and saccharin to a mixing vessel. Disperse the thickening agents, carboxymethyl cellulose and xanthan gum, in the glycerin. Add this mixture of dispersed thickening agents in glycerin to the mixing vessel, mix well, and heat to at least 40° C. Mix the flavor in the Poloxamer and add to the mixture. Add the polyethylene glycol, propylene glycol, and sodium carbonate. Mix well. Next, add the titanium dioxide and the silica. After mixing, add the sodium bicarbonate (if used) and sodium alkyl sulfate. Finally, add the polyphosphate and calcium peroxide (if used). Continue stirring the mixture until homogeneous.

What is claimed is:

1. An oral composition consisting essentially of:
   a. an effective amount of one or more linear polyphosphates having an average chain length of greater than about 6, wherein the linear polyphosphate is the effective anticalculus agent;
   b. from about 0.15% to about 2.28% of sodium monofluorophosphate;
   c. an effective amount of a buffering agent;
   d. from about 6% to about 70% of an abrasive polishing material containing less than 23% calcium; and
   e. from about 50% to about 99% of one or more aqueous carriers;

wherein said oral composition has a total water content of from about 5% to about 20%, has a pH of from about 6.5 to about 10, and is free of ionic fluoride to avoid a reaction between said ionic fluoride and said linear polyphosphate which compromises the ability of said oral composition to provide polyphosphate to the oral surfaces.

2. The oral composition according to claim 1 wherein each of the one or more polyphosphates is in an amount of from about 0.5% to about 20%.

3. The oral composition according to claim 2 wherein each of the one or more polyphosphates is selected from the group consisting of linear "glassy" polyphosphates having the formula $$XO(XPO_3)_nX$$

wherein X is sodium or potassium and n averages from greater than about 6 to about 21.

4. The oral composition according to claim 3 wherein the buffering agent is sodium carbonate.

5. The oral composition according to claim 4 wherein the buffering agent is in an amount of from about 0.1% to about 30%.

6. The oral composition according to claim 5 wherein the abrasive polishing material is selected from the group consisting of silicas, aluminas, phosphates, orthophosphates, polymetaphosphates, and mixtures thereof.

7. The oral composition according to claim 6 further comprising from about 0.5% to about 40% of an alkali metal bicarbonate salt.

8. The oral composition according to claim 7 further comprising from about 0.01% to about 10% of a peroxide source.

9. The oral composition according to claim 8 wherein the peroxide source is calcium peroxide.

10. The oral composition according to claim 9 wherein the total water content is from about 7% to about 14%.

11. The oral composition according to claim 10 wherein the aqueous carriers are materials selected from the group consisting of surfactants, thickening materials, humectants, water, titanium dioxide, flavor systems, sweetening agents, xylitol, coloring agents, and mixtures thereof.

12. A method for reducing the incidence of calculus on dental enamel comprising contacting the enamel surfaces in the mouth with the oral formulation according to claim 1.

13. The oral formulation according to claim 11 wherein the oral composition further comprises one or more antimicrobial agents selected from the group consisting of zinc salts, triclosan, chlorhexidine, flavor oils, and mixtures thereof.

14. A method of improving delivery of linear polyphosphate to oral cavity surfaces by administering an oral composition consisting essentially of:

a. an effective amount of one or more linear polyphosphates having an average chain length of greater than about 6, wherein the linear polyphosphate is the effective anticalculus agent;

b. from about 0.15% to about 2.28% of sodium monofluorophosphate;

c. an effective amount of a buffering agent;

d. from about 6% to about 70% of an abrasive polishing material containing less than 23% calcium; and e. from about 50% to about 99% of one or more aqueous carriers;

wherein said oral composition has a total water content of from about 5% to about 20%, has a pH of from about 6.5 to about 10 and is free of ionic fluoride to avoid a reaction between said ionic fluoride and said linear polyphosphate which compromises the ability of said composition to provide polyphosphate to the oral surfaces.

* * * * *